United States Patent
Clark et al.

[11] 4,010,636
[45] Mar. 8, 1977

[54] VESSEL EXAMINATION SYSTEM

[75] Inventors: Jack Phillip Clark; Thurman Dale Smith; Alan Carl Foster, all of San Jose, Calif.

[73] Assignee: General Electric Company, San Jose, Calif.

[22] Filed: Feb. 23, 1976

[21] Appl. No.: 660,651

Related U.S. Application Data

[62] Division of Ser. No. 540,607, Jan. 13, 1975.

[52] U.S. Cl. ............................................. 73/67.8 S
[51] Int. Cl.² ........................................ G01N 29/04
[58] Field of Search .................. 73/67.8 S, 71.5 US; 144/222; 180/1 VS

[56] References Cited

UNITED STATES PATENTS

| | | | |
|---|---|---|---|
| 3,777,834 | 12/1973 | Hiraoka et al. | 180/1 |
| 3,810,515 | 5/1974 | Ingro | 180/1 |
| 3,811,320 | 5/1974 | Cowell | 73/67.8 |
| 3,850,028 | 11/1974 | Thompson et al. | 73/71.5 |

*Primary Examiner*—Herbert Goldstein
*Attorney, Agent, or Firm*—Ivor J. James, Jr.; Sam E. Laub; Samuel E. Turner

[57] ABSTRACT

A system for on-site, non-destructive examination of the seam welds or other portions of the walls of a vessel, for example, a nuclear reactor pressure vessel, including an instrument carrying, remotely controlled vehicle with magnetic adherence means which may be selectively propelled to any position on the walls of the vessel and including an ultrasonic signal system utilizing a triangulation technique for remotely indicating the position of the vehicle on the vessel.

11 Claims, 8 Drawing Figures

VESSEL EXAMINATION SYSTEM

This is a division of application Ser. No. 540,607, filed Jan. 13, 1975.

BACKGROUND

In some instances it is desirable to provide in-service examination of large pressure vessels to verify the integrity of the vessel or to discover any incipient defects so that appropriate repairs can be made before failure occurs.

In some cases, for example, where the vessel is relatively inaccessable or hazardous to humans, the use of conventional inspection techniques and equipment is precluded. A noteable example is a pressure vessel containment for a nuclear reactor. Such a pressure vessel may be in the order of 60 feet in height and 20 feet in diameter with walls of steel 4 to 12 inches in thickness. In use, such a vessel is exposed to radioactive fields. Furthermore, such vessels are ordinarily closely surrounded by heat insulation and a biological shield wall. These and other factors dictate the provision of remotely operable equipment for the in-service inspection of such vessels.

A method for on-site examination of a nuclear reactor pressure vessel has been described by L. B. Gross et al in U.S. Pat. No. 3,715,914 wherein ultrasonic signal transducers for examining the vessel walls are mounted on a carriage which is movably mounted on tracks at the top and bottom of the sides of the vessel. Use of such an arrangement is difficult unless the surface to be examined is relatively free of obstruction, particularly when there is restricted space between the vessel and surrounding structure such as a shield wall. In many cases a number of pipes of various sizes penetrate the vessel walls, such as feed lines, recirculation lines and the like. A tracked arrangement is not well suited for circumventing such obstructions nor for scanning the area above and below such obstructions.

A tank or vessel scaler device which does not require guide tracks is described by T. E. Cowell et al. in U.S. Pat. No. 3,811,320 wherein independently driven cross-members are selectively held on the vessel wall by selectively actuatable electromagnets whereby the device can be moved stepwise across the vessel surface.

Various vehicles which utilize magnetism for adherence of the vehicle to surfaces have been proposed for a variety of purposes and are shown, for example, by J. D. Hilliard in U.S. Pat. No. 1,262,341; by J. W. Allen in U.S. Pat. No. 2,030,840; by Michito Hiraoku in U.S. Pat. No. 3,777,834.

In general, prior devices are found inadequate or limited in their capability for providing the desired degree of accuracy, versatility or ease of operation in the in-service examination of restricted access vessels.

It is an object of the present invention to provide a system for the remotely controlled examination of the walls of a vessel including a vehicle which may be propelled, around obstacles where necessary, to any position on the vessel and wherein the position of the vehicle is determined with a high degree of accuracy.

SUMMARY

This and other objects of the invention are achieved by providing a system including a vehicle fitted with electric motor driven magnetic wheels, the wheels on each side being separately driveable by which the vehicle can be steered.

Ultrasonic signal transducers for transmitting signals into and receiving reflected signals from the vessel material are fastened to a carriage or bracket which, in turn, is translatably supported on a guide frame or track supported by the vehicle by which the transducers may be selectively moved across the surface of the vessel in a direction transverse to the longitudinal axis of the vehicle whereby a path is scanned across the vessel.

The location of the vehicle on the vessel is accurately determined by an acoustic signal arrangement employing a triangulation technique including an acoustic signal transmitter mounted on the vehicle and at least three acoustic signal receiving transducers mounted at known spaced locations on the vessel.

Other features of the system of the invention include a turning electromagnet mounted on the vehicle to provide a precise pivot point when turning the vehicle, a pendulum operated indicator for indicating the attitude or azimuth of the vehicle with respect to the vertical surface of the vessel, an independent odometer wheel coupled to an indicator or odometer for indicating distance of vehicle travel and an independent castor wheel coupled to an indicator for indicating the degree of offset of the caster wheel with respect to the longitudinal axis of the vehicle as an indication of turning of the vehicle.

DRAWINGS

Other features and further details of the invention are described hereinafter with reference to the accompanying drawing wherein.

DESCRIPTION

Figure 1:
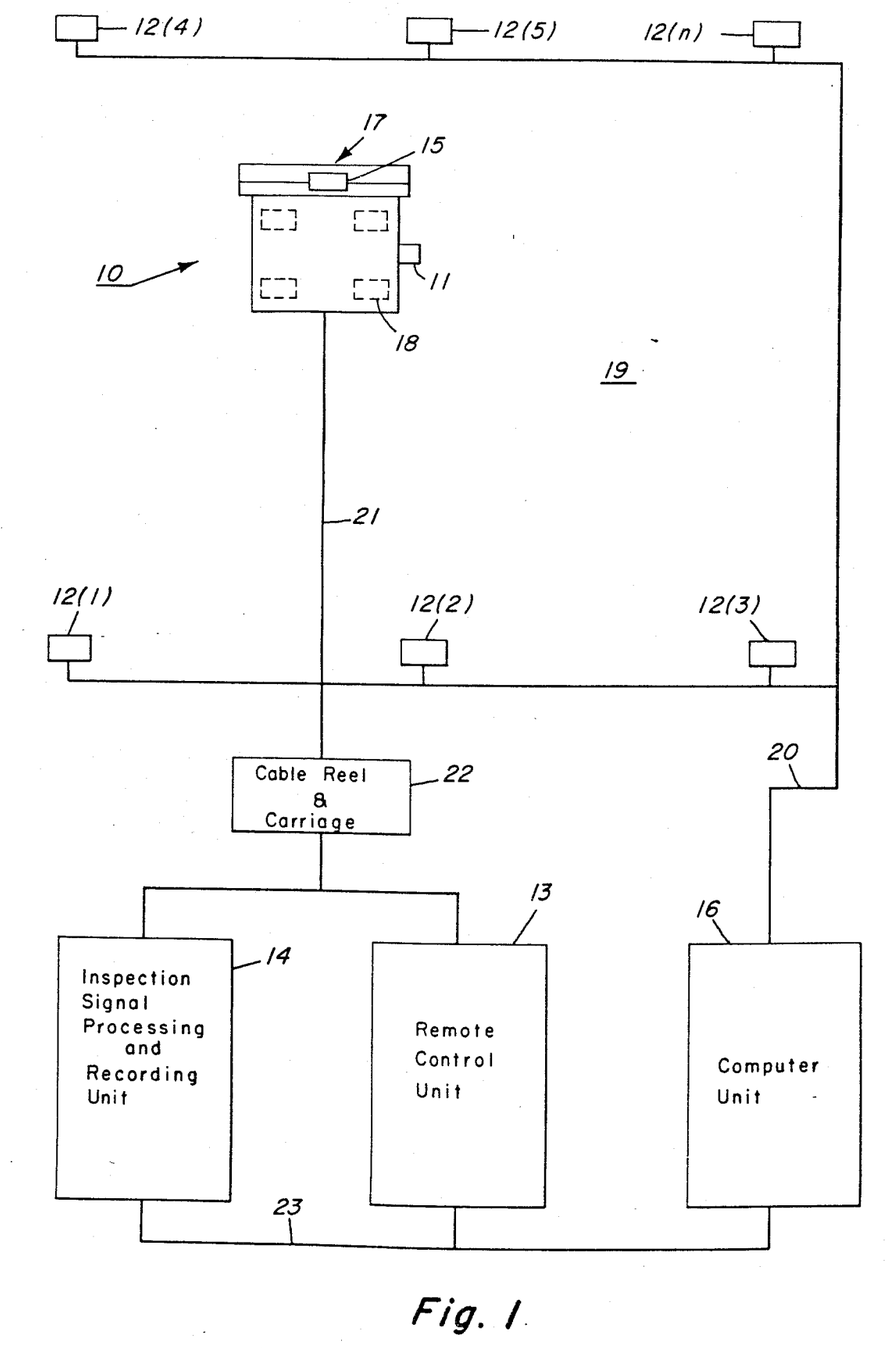
FIG. 1 is a schematic diagram of the system of the invention.

The system of the invention is broadly illustrated by the schematic diagram of FIG. 1. The system includes a vehicle 10, a vehicle location signal transmitting transducer or transmitter 11 mounted on the vehicle, a plurality of vehicle location signal receiving transducers or receivers 12(1) – 12(n), a vehicle remote control unit 13, an inspection signal processing and recording unit 14 and a computer unit 16.

Vessel inspection transducers are attached to a carriage or bracket 15 movably mounted on a transverse guide or track 17 supported by the vehicle 10 and means are provided to selectively more carriage 15 back and forth to scan a path on the vessel to be examined in a direction transverse to the longitudinal axes of the vehicle 10. The vehicle 10 is fitted with magnetic wheels 18 for adherence of the vehicle to the vertical walls of the vessel (indicated generally as 19) the wheels being driven by selectively energizable electric motors by which the vehicle can be propelled and guided or steered. (Details of the vehicle will be described hereinafter with reference to FIG. 4.)

A cable of electrical wires 20 connects the location receiver transducers 12(1) – 12(n) to the computer 16. A trailing remote control cable of electrical wires 21 is connected between the vehicle 10, a cable reel and carriage device 22 and the units 13 and 14; and a cable of wires 23 provides electrical and signal interconnection between the units 13 and 14 and the computer unit 16.

The acoustic signal vehicle location receiving transducers or receivers 12(1) – 12(n) are located near the top and bottom of the vertical walls of the vessel or at other convenient spaced locations. Since the acoustic signal from the transmitting transducer 11 suffers attenuation in its propagation through the vessel material, a sufficient number of receivers 12(1) – 12(n) are used so that in any position of the vehicle 10 on the portion of the vessel under examination the closest three (or other selected number) of the receivers 12(1) – 12(n) will receive signals of sufficient strength. (The transducers 12(1) – 12(n) conveniently may be removably secured to the vessel by, for example, suitable permanent magnets.)

Figure 2A:
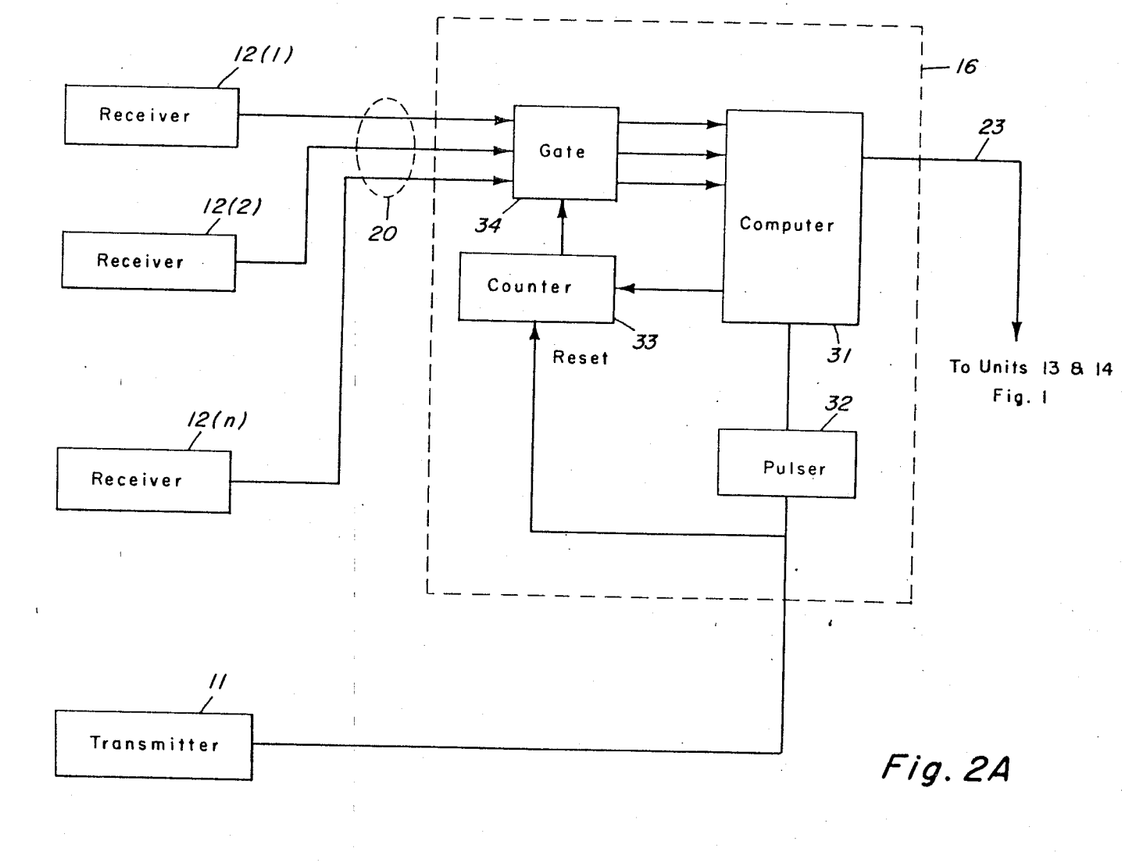
FIG. 2A is a schematic illustration of the triangulation arrangement used for determination of vehicle location.

Operation of the vehicle location arrangement is as follows, with reference to the schematic diagram of FIG. 2A and the example illustrated by FIGS. 2B and 2C.

Under manual control from the control unit 13 or under automatic control from a computer 31 or computer unit 16, the transmitter 11 periodically transmits (for example, by actuation of a pulser 32) a timed pulse or burst 24T of acoustic signal, for example, having a frequency of 350 KHz, into the material of the vessel wall (for example, steel) at a time $t_0$.

This acoustic signal is transmitted through the vessel walls at a velocity depending on the propagation characteristics of the vessel material. This velocity is known or can be determined by routine experiment.

Figure 2B:
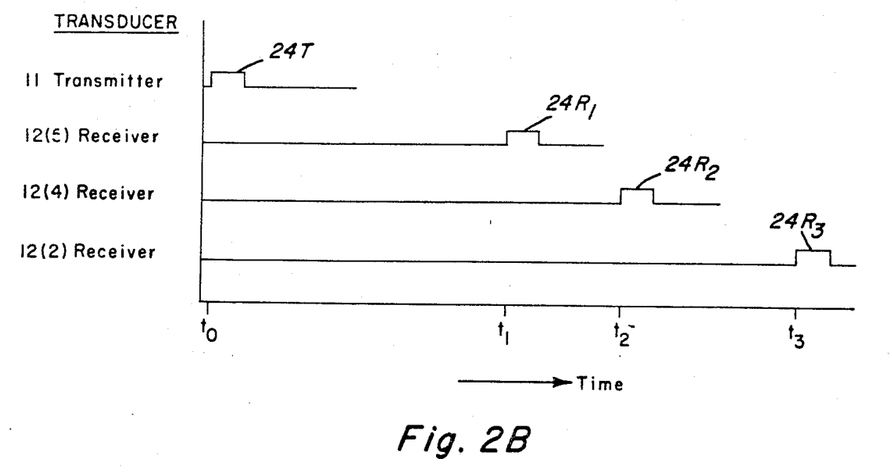
FIG. 2B is a timing diagram and FIG. 2C is a sketch of an example of the vehicle location technique.
Figure 2C:
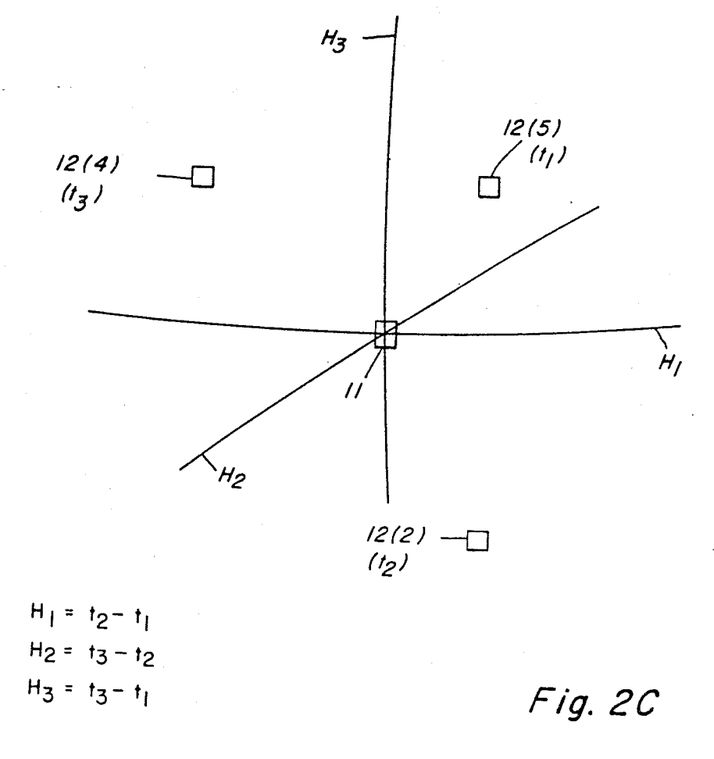

Thus this acoustic signal pulse will be received by receiving transducers 12(1) – 12(n) at times dependent upon the distance of the particular receiving transducers from the vehicle 10 as illustrated in FIG. 2B. As shown in FIG. 1, the receiver 12(5) is closest to the transmitter 11, therefore, it is first to receive, at a time $t_1$, the transmitted location signal as a received signal $24R_1$. Receivers 12(4) and 12(2), being more remote, receive the location signal, at time $t_2$ and $t_3$, as received signals $24R_2$ and $24R_3$.

The transmitted signal 24T is also received by the other receivers at later times; however, it is a feature of the present location arrangement that only the first three (or other predetermined number) of the received signals are used for vehicle location determination. This may be accomplished, for example, by a counter 33 which counts the received signals and disables a gate 34 after the predetermined number of signals are received, thus gating off subsequent signals during the remainder of the particular vehicle location determination period. The counter 33 may be reset by the transmitter actuation pulse from pulser 32 at the beginning of the next location determination period.

Thus from the known locations of the receivers 12(1) – 12(n) and the times $t_1$, $t_2$ and $t_3$, the location of the vehicle 10 can be determined by a standard graphical technique generally known as triangulation. For example, one calculational method of performing such triangulation is as follows with reference to FIG. 2C: As illustrated in FIG. 2B, $t_1 < t_2 < t_3$. First, calculate a line $H_1$, a hyperbola all points of which equal $t_2-t_1$ for any position of the vehicle along the line $H_1$. That is, the origin of the transmitted signal 24T is somewhere along this line. Next, calculate a line $H_2$, a hyperbola all points of which equal $t_3-t_2$. As illustrated in FIG. 2C, the lines $H_1$ and $H_2$ define the location of the transmitter 11 (and hence the vehicle 10). However, in general, the lines $H_1$ and $H_2$ may have two intersections, either of which may represent the vehicle position. Thus, finally, calculate a third line $H_3$, a hyperbola all points of which equal $t_3-t_1$. This resolves any ambiguity and the location of the vehicle 10 is the common intersection of lines $H_1$, $H_2$ and $H_3$. By this or other known calculational method the computer 31, suitably programmed, can perform the vehicle position calculation and provide a vehicle position signal over cable 23 to units 13 and 14 for storage and display as desired.

As described above, time $t_0$ is a reference time based upon the transmitted acoustic signal pulse 24T. Other reference times can be used. For example, a reference time can be taken as the time that the transmitted pulse 24T is first received by one of the receiving transducers 12(1) – 12(n) and the triangulation can then be accomplished with reference to this time from the subsequent times that the transmitted pluse is received at the next three receiving transducers.

Figure 3:
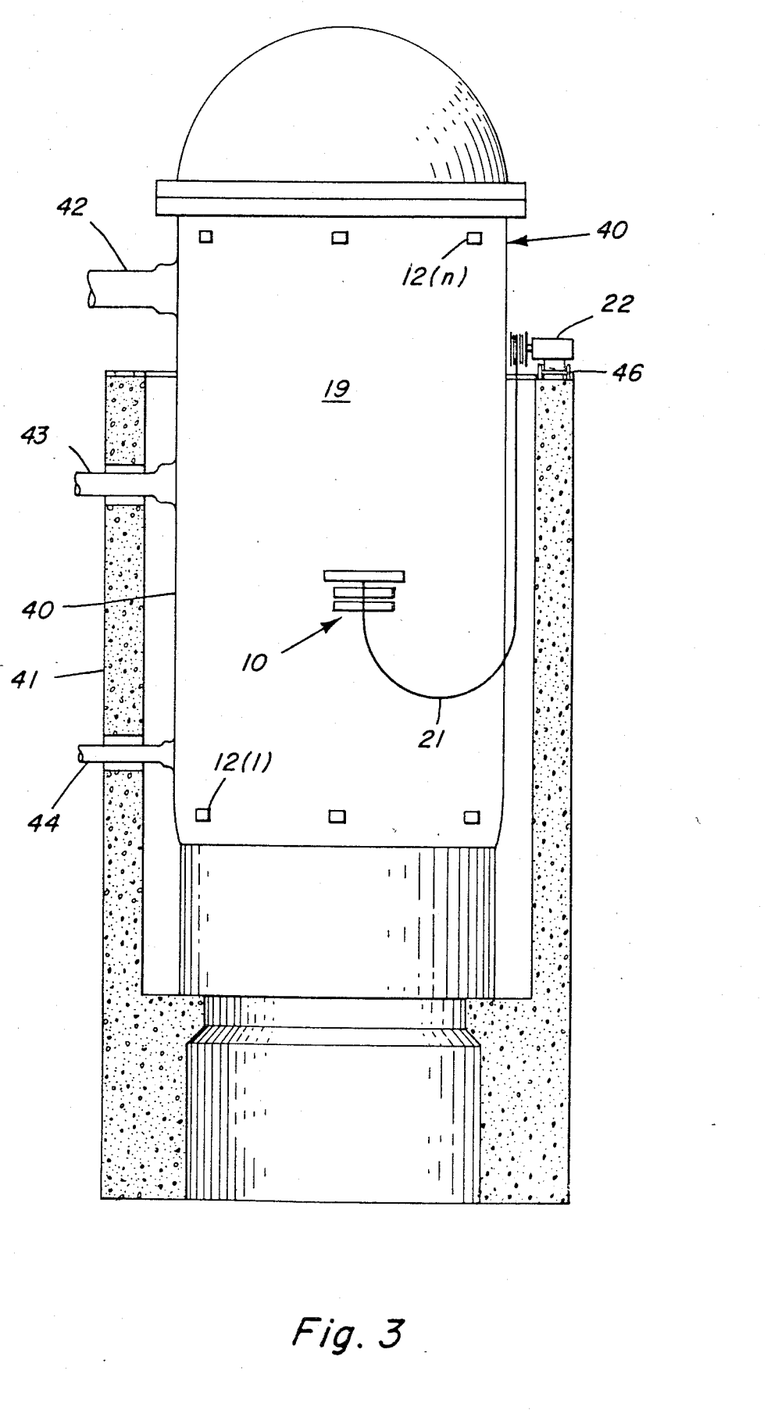
FIG. 3 is an elevation view, partly in section of a typical pressure vessel surrounded by a shield wall.

Illustrated in FIG. 3 is a typical large pressure vessel 40 formed of thick steel plates welded together. The vehicle 10 is schematically shown on the vertical walls 19 of the vessel. The vessel 40 is surrounded by a biological shield wall 41 formed, for example, of concrete which may be spaced from the vessel by as little as 8 or as much as 36 inches. The walls 19 of the vessel 40 are penetrated by a plurality of pipes of various sizes such as pipes 42, 43 and 44 which present obstructions that must be circumvented by the vehicle 10.

Receivers 12(1) – 12(n) are shown positioned near the top and bottom of the wall 19; however, the receivers can be placed in any convenient location of wall 19 spaced around the area in which the vehicle 10 is to scan.

For ease of handling and to minimize the weight of remote control cable 21 on the vehicle 10, it is preferably to provide a cable reel and carriage arrangement 22 conveniently mounted for example, on tracks 46 atop the shield wall 41. The cable reel and carrige 22 (not described in detail) may be any suitable device capable of operating under remote control to pay out or take up the cable 21 as required as the vehicle 10 is maneuvered across the vehicle wall 19.

Figure 4:
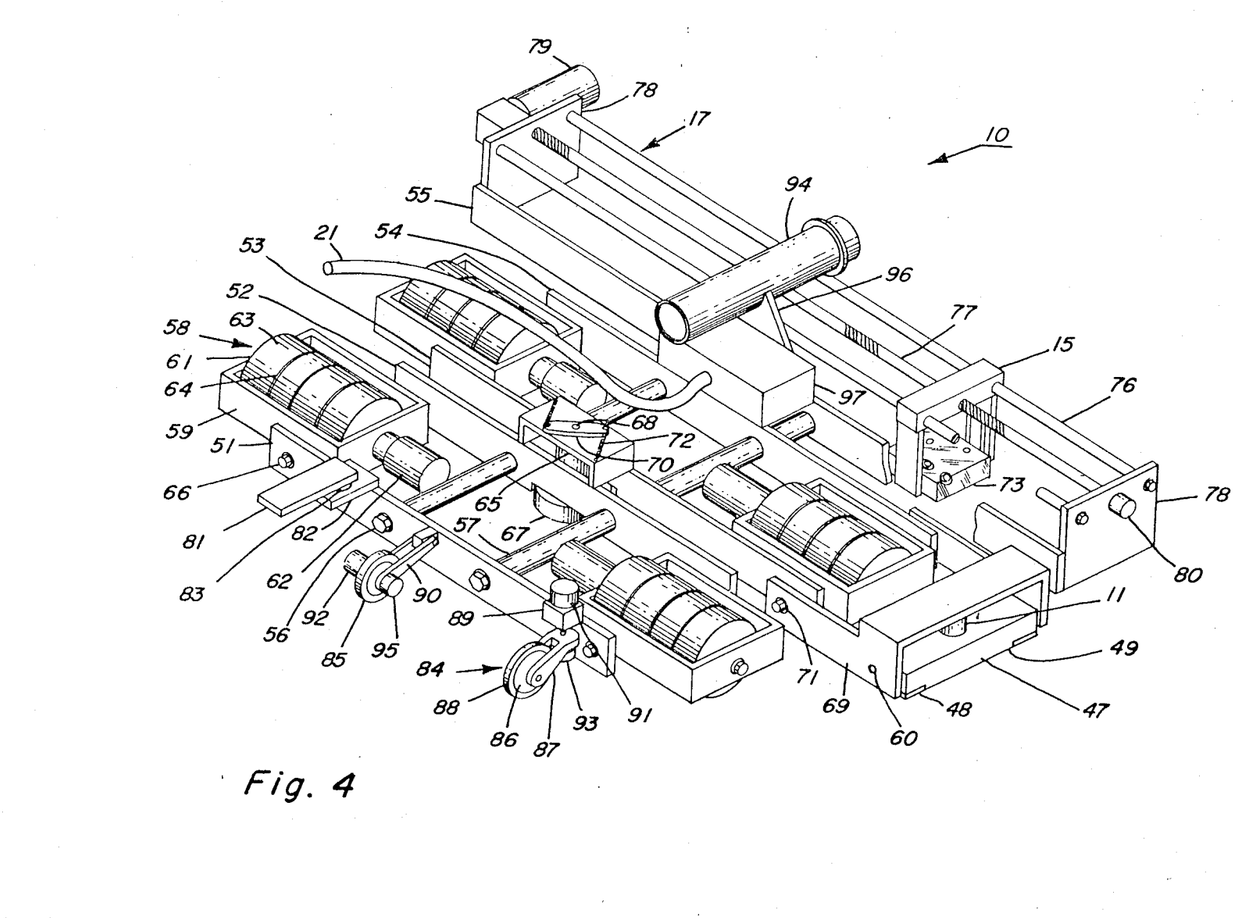
FIG. 4 is a perspective view of the vehicle of the system of the invention.

The remotely controlled vehicle 10 is illustrated in FIG. 4. As shown therein a vehicle frame is comprised of a plurality of bars 51–55 fastened together in spaced parallel relation by tie rod and spacer members 56 and 57. (To the extent feasible, the frame members, bracket and carriage members, etc., are preferably formed of light-weight non-magnetic material such as aluminum.)

The vehicle 10 is supported by four magnetic wheel units 58. Each wheel unit includes a rectangular frame 59, a magnetic wheel 61 having an axle journalled for rotation in frame 59, and an electric motor 62 coupled to drive the wheel 58.

The wheels 58 contain permanent magnets and are formed, for example, with a plurality of annular pole pieces 68 separated by spacers or washers 64 of non-magnetic material such as aluminum. The adjacent ends of pole pieces 63 are of opposite poles so that strong magnetic fields are developed across the spacer washers 64.

The wheel frames 59 are pivotally attached to the vehicle framework, for example, the left-rear wheel frame 59 is attached to spaced frame bars 51 and 52 by pivot pins such as pivot pin 66. This allows the wheels 58 to maintain as flat a position as possible against the cylindrical surface of the vessel and greatly increases the adherence of the vehicle to the vessel as compared to wheels rigidly mounted to a frame.

Since each wheel 61 is provided with an individual drive motor 62, the vehicle readily may be steered or turned by actuation of the drive motors on one side or the other or by reversing the motors on one side as desired.

To provide a definite and known pivot point and to aid in making large degree turns, a selectively energizeable electromagnet 67 is provided. Electromagnet 67 is attached to a shaft 68 which is journalled for rotation in a bracket 65. The bracket 65 is supported on frame members 52 and 53. A pair of springs 72, attached between the bracket 69 and the ends of a double arm 70, secured to shaft 68, return the electromagnet 67 to its initial position upon de-energization thereof.

The vehicle location transducer or transmitter 11 is mounted in a transducer block 47 (formed of non-magnetic material such as plastic) pivotally supported with a pair of pins 60 by a bracket 69, the bracket 69 being pivotally attached to the frame members 53 and 54 by a pair of pivot pins 71. To assure consistent contact of the contacting face 49 of transducer block 47 with the vessel wall 19 (and hence good coupling of the transmitter 11), the face 49 is fitted at its four corners with permanent magnets 48.

At its forward end, the vehicle 10 supports a vessel scanning arrangement. Suitable vessel examination transducers are fitted in a transducer block 73 attached to the carriage 15. (Details of the block 73 and carriage 15 are described hereinafter with reference to FIG. 5.)

The carriage 15 is mounted on the track or guide arrangement 17 which includes one or more guide rods 76 and an elongated drive screw 77, the drive screw 77 engaging a threaded portion of the carriage 15 by which rotation of the screw 77 can drive the carriage 15, and hence the transducer block 73, back and forth, in a direction transverse of the longitudinal axis of the vehicle 10 whereby the transducers in block 73 can scan a path across the surface of the vessel. The guide rods 76 and drive screw 77 are supported by a pair of end plates 78 which are secured to frame bar 55. A reversible electric drive motor 79 is geared to drive screw 77 for selective rotation thereof. A suitable rotation encoder 80 attached to the right-hand end plate 78 is driven by the screw 77 to indicate rotation of the screw 77 and hence the position of the carriage 15.

To provide an indication of the attitude or azimuth of the vehicle on the verticle walls of the vessel, a pendulum 81 is pivotally attached to a bracket 82 fixed to frame bar 51. The pendulum 81 drives a suitable position encoder 83, for example, a potentiometer or other suitable position sensitive device.

The vehicle 10 is also provided with a caster wheel assembly 84 to indicate turning of the vehicle. The caster wheel assembly 84 includes a caster wheel 86 journalled in a caster arm and axle unit 87. The caster wheel 86 contains permanent magnet means, for example, a permanent magnet tire 88, to provide adherence of the wheel 86 to the vessel. The caster axle is journalled in a bracket 89 (fixed to frame bar 51) with sufficient spacing to assure continuous contact of the wheel 86 with the vessel surface irrespective of changes in the distance between the bar 51 and the vessel surface.

The caster axle drives a suitable position encoder 91 (for example, a potentiometer) which provides an electrical indication of the position of the caster wheel with respect to the longitudinal axis of the vehicle. Coupled to the caster axle a selectively actuatable brake 93 is provided to prevent change in position of the caster wheel when desired, for example, when the vehicle is driven in the reverse direction.

Also provided in a magnetic odometer wheel 85 pivotally attached to the vehicle 10 by arms 90. An odometer or distance travel encoder 92 (of known suitable type) is driven by the axle of the odometer wheel 85 to provide an indication of the distance of vehicle travel. A selectively actuable brake 95 is also provided by which rotation of the odometer wheel 85 can be prevented when desired, for example, to maintain the reading of the odometer 92 during vehicle turns.

The vehicle 10 may also carry other desirable instruments, for example, a television camera 94 supported on the vehicle by a bracket 96.

An enclosure 97 is provided as a housing for terminal boards, relays, preamplifiers and the like and as a terminus for the remote control cable 21. The cable 21 contains the necessary electrical power, control and signal conductors. It also includes a flexible tube for providing coupling fluid for transmitting transducer 11 and the vessel inspection transducers in transducer block 73. For clarity of the drawing, the connections from cable 21 to the various devices on vehicle 10 are not shown.

Figure 5:
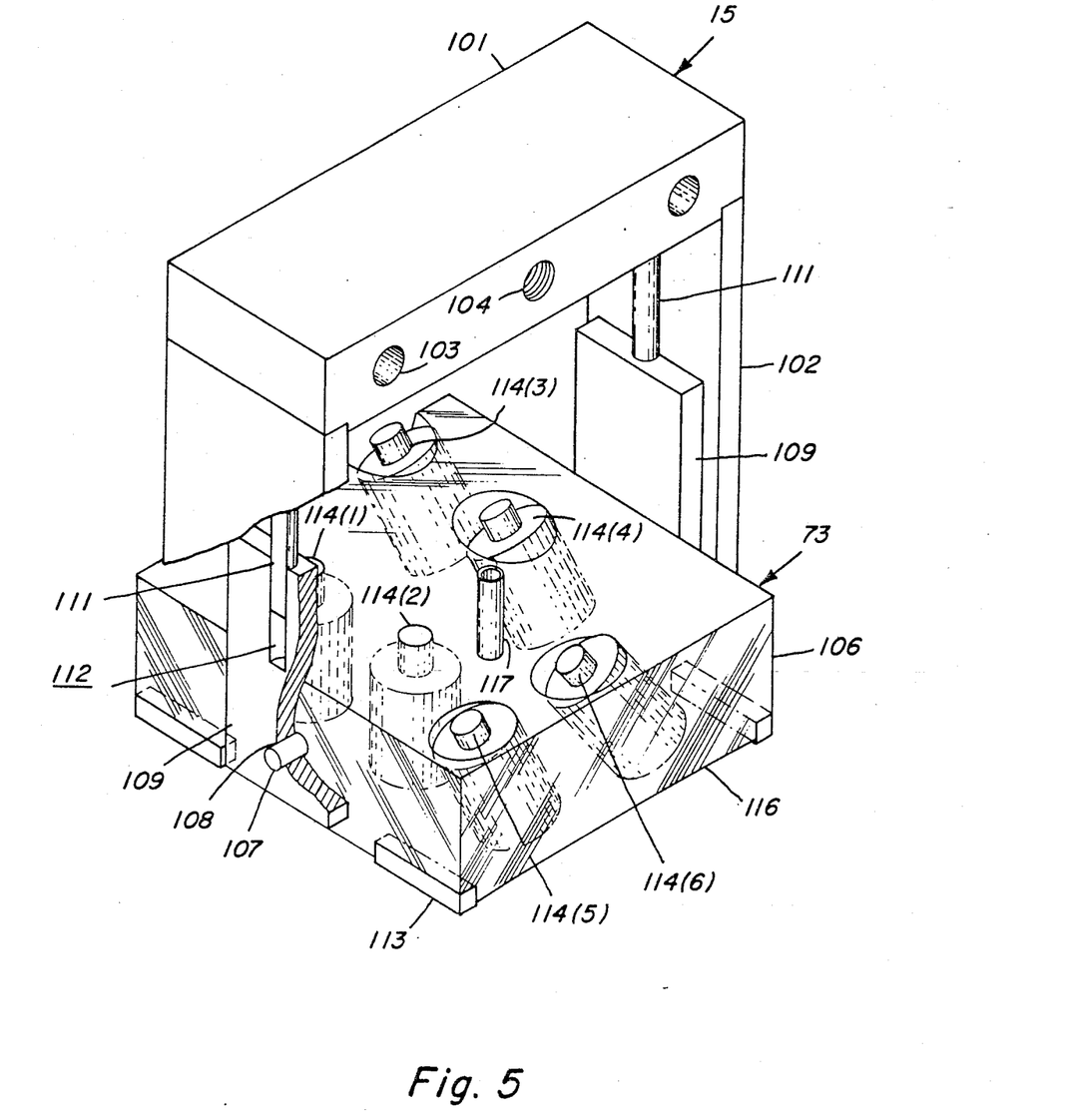
FIG. 5 is a perspective view of the vessel inspection transducer block and carriage.

The vessel inspection transducer block 73 and its carriage 15 are shown in FIG. 5. The carriage 15 includes a transverse member 101 to which is attached side members 102 to thus form an inverted U-shaped carriage. The member 101 is formed with holes 103 through which the guide rods 76 (FIG. 4) extend. Holes 103 may be fitted with suitable bushings (not shown). The member 101 is also formed with a hole 104 which may be threaded or fitted with a threaded bushing or nut to receive the drive screw 77 (FIG. 4).

The transducer block 73 includes a body 106 formed of non-metallic material such as a suitable plastic. The body 106 is pivotally attached to the carriage 15 by an arrangement which also allows limited relative movement between the carriage 15 and transducer block 73. This arrangement includes a pair of pivot pins, such as a pivot pin 107 secured to and extending from opposite sides of the body 106. The pins 107 are journalled in bores 108 in a pair of connecting blocks 109.

Fixed to the inside surfaces of side members 102 and respective guide bars 111 and the connecting blocks 109 are formed with mating grooves 112 by which the guide bars 111 are slideably engaged. With this arrangement the transducer block 73 is free to follow the contour of a curved vessel wall under inspection.

Fitted in cavities in the body 106 of transducer block 73 is a plurality of suitable vessel inspection transducers 114(1) – 114(6). Transducers 114(1) and 114(2) may be perpendicular to the face 116 of the body 106 (and hence substantially perpendicular to the surface of the vessel). Transducers 114(3) and 114(4) may be oriented at different angles from the face 116 in the direction of travel of the carriage 15 and block 73;

while the transducers 114(5) and 114(6) may be oriented at different angles transverse to the direction of travel of carriage 74. For example, transducers 144(3) and 114(5) may be oriented about 45° (from the perpendicular) while the transducers 114(4) and 114(6) may be oriented about 60° (from the perpendicular). Thus, for example, in examining the weld seams of the vessel, one of the transducers 114(1) and 114(2) can be used to examine the base metal and the other can be used to examine the weld in a perpendicular direction while the transducers 114(3) – 114(6) can be used to examine the weld seam from two different directions at two different angles.

To assure close contact between the transducer block 73 and the vessel wall, and hence good coupling of the transducers 114(1) – 114(6), the body 106 is fitted, at the corners of the face 116, with permanent magnets 113.

Additionally, a tubular fitting 117 attached to the body 106 is provided for connection to a hose (not shown) by which a suitable acoustic signal coupling fluid (for example, water) may be fed through suitable channels (not shown) in the body 106 to the faces of the transducers 114(1) – 114(6).

The transducers 114(1) – 114(6) are operated in the well-known "pulse-echo" manner, that is, each transducer operates as both a transmitter of pulses of acoustic signal and as a receiver of reflections back to the transducer of such signals. (As is well-known, flaws or discontinuities in the vessel metal are detected by the time and nature of the reflected signals.)

A method of operation of the system, for example, in the inspection of the seam welds of vessels wall 19 is as follows with reference particularly to the diagram of the system of FIG. 19. It is contemplated that an accurately dimensioned map of wall 19 will have been prepared before or during installation of the vessel 40 and further that at least one index mark, such as an acoustically detectable indentation, has been placed on the vessel in a convenient known location. With reference to the index mark the vehicle 10 is propelled and guided to the weld seam to be examined with the vehicle location transmitter 11 positioned over the weld seam. The location transmitter 11 is then pulsed and the vehicle location is determined and displayed and recorded as described hereinbefore.

Starting at a known position (as indicated by encoder 80) the carriage 15 and hence the transducer block 73, is moved in discrete steps along the carriage guide 17. At each such step, the vessel inspection transducers 114(1) – 114(6) are sequentially pulsed with an acoustic signal, of a frequency of 2.25 MHz, for example, and the reflected signals from these pulses are received and recorded in known manner.

After the carriage 15 has been thus stepped over a desired distance on guide 17, the drive motors of the vehicle 10 are actuated to drive the vehicle forward (or backward) to thus present another (preferably overlapping) scanning path for the vehicle inspection transducers. The vehicle location transmitter 11 is again pulsed, etc., to start another operating cycle. It is further contemplated that this inspection procedure can be carried out both manually and automatically under computer control.

Thus what has been described is a system for examining the walls of a vessel including a remotely controlled vehicle with position determining means which can be propelled to any selected position of the vessel wall.

What is claimed is:

1. A magnetically adherent trackless vehicle adapted to be remotely propelled and steered over the surface of a magnetic body including curved surfaces thereof, comprising: a frame having a longitudinal axis; a pair of spaced wheels mounted to each of two opposite sides of said frame for supporting said vehicle on said surface, each of said wheels containing magnetic means in the form of permanent magnets for providing adherence of said vehicle to said vessel, each of said wheels being rotatably attached to one end of a suspension bracket extending generally laterally outward from said frame, the other end of said suspension bracket being pivotally attached to said frame whereby said wheels can maintain as flat a position as possible against said surface for increased adherence to curved surfaces thereof; separate electric drive motors coupled to the wheels on said opposite sides of said frame; said drive motors being separately and remotely energizable for propelling and steering said vehicle over said surface.

2. The vehicle according to claim 1 wherein each of said wheels is formed of a plurality of permanent magnets and a plurality of spaced annular pole pieces whereby the magnetic force is concentrated at the spaces between adjacent ends of said pole pieces.

3. The vehicle according to claim 2 wherein said pole pieces are spaced by washers formed of non-magnetic material.

4. The vehicle according to claim 1 further including a pivot electromagnet mounted on said frame adjacent to said surface, said electromagnet being selectively energizable to serve as a pivot point for and to aid in adherence of said vehicle to said surface during turning of said vehicle.

5. The vehicle according to claim 1 wherein the pivot axes of said suspension brackets are substantially parallel to the longitudinal axis of said frame.

6. The vehicle according to claim 1 further including a pendulum pivotally attached to said frame and means operated by said pendulum for indicating the position of said pendulum with respect to said frame.

7. The vehicle according to claim 1 further including a caster wheel including a caster axle for pivotally mounting said caster wheel on said frame for rotation over said surface upon movement of said vehicle over said surface and means operated by said caster axle for indicating the position of said caster wheel with respect to said frame.

8. The vehicle according to claim 7 wherein said caster wheel is formed with permanent magnet means to maintain contact of said wheel with said surface of said magnetic body.

9. The vehicle according to claim 8 further including a brake for said caster wheel, said brake being selectively operable to prevent change in position of said caster wheel.

10. The vehicle according to claim 1 further including an odometer wheel mounted on said frame for rotation over said surface and odometer means connected to said odometer wheel and responsive to rotation thereof to provide an indication of the distance of travel of said vehicle over said surface.

11. The vehicle according to claim 1 including scanning means mounted on said frame in proximity to said surface for examining local portions of said body.

* * * * *